United States Patent
Tran et al.

(10) Patent No.: US 9,402,996 B2
(45) Date of Patent: Aug. 2, 2016

(54) RF SHIELD FOR AN IMPLANTABLE LEAD

(71) Applicant: Cardiac Pacemakers, Inc., St. Paul, MN (US)

(72) Inventors: Binh C. Tran, Minneapolis, MN (US); Joseph Walker, Shoreview, MN (US); Greg P. Carpenter, Centerville, MN (US); Jack Gordon, Minneapolis, MN (US)

(73) Assignee: Cardiac Pacemakers, Inc., St. Paul, MA (US)

( * ) Notice: Subject to any disclaimer, the term of this patent is extended or adjusted under 35 U.S.C. 154(b) by 0 days.

(21) Appl. No.: 14/619,460

(22) Filed: Feb. 11, 2015

(65) Prior Publication Data

US 2015/0224303 A1 Aug. 13, 2015

Related U.S. Application Data

(60) Provisional application No. 61/938,368, filed on Feb. 11, 2014.

(51) Int. Cl.
*A61N 1/00* (2006.01)
*A61N 1/08* (2006.01)
*A61N 1/05* (2006.01)
*A61N 1/37* (2006.01)

(52) U.S. Cl.
CPC *A61N 1/08* (2013.01); *A61N 1/056* (2013.01); *A61N 1/3718* (2013.01); *A61N 2001/086* (2013.01)

(58) Field of Classification Search
USPC ..................................................... 607/36, 119
See application file for complete search history.

(56) References Cited

U.S. PATENT DOCUMENTS

| | | | |
|---|---|---|---|
| 4,131,759 | A | 12/1978 | Felkel |
| 4,484,586 | A | 11/1984 | McMickle et al. |
| 5,554,139 | A | 9/1996 | Okajima |
| 5,800,496 | A | 9/1998 | Swoyer et al. |
| 5,954,760 | A | 9/1999 | Jarl |
| 6,143,013 | A | 11/2000 | Samson et al. |

(Continued)

FOREIGN PATENT DOCUMENTS

| | | |
|---|---|---|
| EP | 0092798 A1 | 11/1983 |
| EP | 2429637 B1 | 3/2012 |

(Continued)

OTHER PUBLICATIONS

International Search Report and Written Opinion issued in PCT/US2008/085518 on Oct. 29, 2009, 15 pages.

(Continued)

*Primary Examiner* — Nicole F Lavert
(74) *Attorney, Agent, or Firm* — Faegre Baker Daniels LLP

(57) ABSTRACT

Various embodiments concern shielding an implantable lead from RF energy associated with MRI scans. The lead can include a distal region, a proximal region, an intermediate region between the distal region and the proximal region, at least one electrode disposed on the distal region, and at least one conductor extending from the proximal region to the at least one electrode. Implanting of the lead can include coiling a portion of the intermediate region to define one or more loops and selectively shielding the one or more loops of the lead with a RF shield. The RF shield can comprise metallic material and can be configured to reduce RF signal coupling to the at least one conductor along the one or more loops.

20 Claims, 7 Drawing Sheets

(56) References Cited

U.S. PATENT DOCUMENTS

| | | |
|---|---|---|
| 6,671,554 B2 | 12/2003 | Gibson et al. |
| 6,876,886 B1 | 4/2005 | Wang |
| 6,980,865 B1 | 12/2005 | Wang et al. |
| 7,013,180 B2 | 3/2006 | Dublin et al. |
| 7,015,392 B1 | 3/2006 | Dickenson |
| 7,123,013 B2 | 10/2006 | Gray |
| 7,138,582 B2 | 11/2006 | Lessar et al. |
| 7,174,219 B2 | 2/2007 | Wahlstrand et al. |
| 7,174,220 B1 | 2/2007 | Chitre et al. |
| 7,388,378 B2 | 6/2008 | Gray et al. |
| 7,410,485 B1 | 8/2008 | Fink et al. |
| 7,551,966 B2 | 6/2009 | MacDonald |
| 8,244,346 B2 | 8/2012 | Foster et al. |
| 8,275,464 B2 | 9/2012 | Li et al. |
| 8,538,551 B2 | 9/2013 | Li et al. |
| 8,630,718 B2 | 1/2014 | Stahmann et al. |
| 8,666,513 B2 | 3/2014 | Ameri et al. |
| 8,958,889 B2 | 2/2015 | Walker et al. |
| 2003/0014080 A1 | 1/2003 | Baudino |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144705 A1 | 7/2003 | Funke |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0162600 A1 | 8/2004 | Williams |
| 2004/0210289 A1 | 10/2004 | Wang et al. |
| 2005/0065587 A1 | 3/2005 | Gryzwa |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0283167 A1 | 12/2005 | Gray |
| 2006/0030774 A1 | 2/2006 | Gray et al. |
| 2006/0041294 A1 | 2/2006 | Gray |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2007/0106332 A1 | 5/2007 | Denker et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2008/0023010 A1 | 1/2008 | Inman et al. |
| 2008/0033497 A1 | 2/2008 | Bulkes et al. |
| 2008/0129435 A1 | 6/2008 | Gray |
| 2008/0132985 A1 | 6/2008 | Wedan et al. |
| 2008/0195186 A1 | 8/2008 | Li et al. |
| 2008/0262584 A1 | 10/2008 | Bottomley et al. |
| 2009/0149920 A1 | 6/2009 | Li et al. |
| 2009/0149934 A1 | 6/2009 | Ameri et al. |
| 2009/0171421 A1 | 7/2009 | Atalar et al. |
| 2010/0036466 A1 | 2/2010 | Min et al. |
| 2011/0160819 A1 | 6/2011 | Kunkel et al. |
| 2012/0130453 A1 | 5/2012 | Stahmann et al. |
| 2012/0290053 A1* | 11/2012 | Zhang .................. A61N 1/0558 607/116 |
| 2012/0323297 A1 | 12/2012 | Li et al. |
| 2014/0018896 A1 | 1/2014 | Li et al. |
| 2015/0224303 A1 | 8/2015 | Tran et al. |

FOREIGN PATENT DOCUMENTS

| | | |
|---|---|---|
| EP | 2224995 B1 | 11/2015 |
| JP | 58192205 A | 11/1983 |
| JP | 8308934 A | 11/1996 |
| JP | 2003047653 A | 2/2003 |
| JP | 2004141679 A | 5/2004 |
| JP | 2005515854 A | 6/2005 |
| WO | WO2005081784 A2 | 9/2005 |
| WO | 2006031317 A2 | 3/2006 |
| WO | WO2007047966 A2 | 4/2007 |
| WO | WO2009100003 A1 | 8/2009 |
| WO | 2015123249 A1 | 8/2015 |

OTHER PUBLICATIONS

International Search Report and Written Opinion issued in PCT/US2008/085533, mailed Aug. 26, 2010.

International Search Report and Written Opinion issued in PCT/US2008/087068 on Aug. 3, 2009.

International Search Report and Written Opinion issued in PCT/US2011/052684, mailed Jan. 25, 2012, 11 pages.

International Search Report and Written Opinion issued in PCT/US2015/015336, mailed Jul. 10, 2015, 14 pages.

Invitation to Pay Additional Fees and Partial Search Report, dated Aug. 17, 2009, issued in PCT/US2008/085533, 6 pages.

Partial International Search Report issued in PCT/US2015/015336, mailed May 4, 2015, 2 pages.

* cited by examiner

RF SHIELD FOR AN IMPLANTABLE LEAD

CROSS-REFERENCE TO RELATED APPLICATION

This application claims priority to Provisional Application No. 61/938,368, filed Feb. 11, 2014, which is herein incorporated by reference in its entirety.

TECHNICAL FIELD

The present disclosure relates to implantable medical devices. In particular, embodiments of the present disclosure relate to MRI conditionally safe lead features.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to one or more conductive leads each having one or more electrodes that can be used to sense bioelectrical cardiac signals and deliver pacing therapy and/or electrical shocks to the heart. In atrioventricular (AV) pacing, for example, the leads are usually positioned in a ventricle and atrium of the heart, and are attached via lead terminal pins to a pacemaker or defibrillator which is implanted pectorally or in the abdomen.

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3.0 Teslas. The RF fields generated in an MRI environment can induce currents in conductive elements. Currents may be inducted by RF fields in an elongated conductor (e.g., a cable) along an insulated section of a lead and then conducted to a non-insulated element (e.g., a stimulating coil or electrode) of the lead that contacts the patient's tissue. The inducted MRI energy may then convert to heat energy when dissipating to the patient's tissue at the electrode/tissue interface. If high enough in temperature, the heating caused by the dissipating energy may be harmful to the tissue that is adjacent to the lead. The degree of tissue heating is typically related to factors such as the length of the lead, the conductivity or impedance of the lead, and the surface area of the lead electrodes.

SUMMARY

The various embodiments of the present disclosure relate to features of implantable electrical leads including an RF shield.

In example 1, a method of shielding an implantable lead includes implanting a lead in a patient, the lead having a distal region, a proximal region, an intermediate region between the distal region and the proximal region, at least one electrode disposed on the distal region, and at least one conductor extending from the proximal region to the at least one electrode. The method can further include coiling a portion of the intermediate region to define one or more loops. The method can further include selectively shielding the one or more loops of the lead with a RF shield, the RF shield comprising metallic material and configured to reduce RF signal coupling to the at least one conductor along the one or more loops.

In example 2, the method according to example 1, wherein the RF shield comprises a metallic bag, and selectively shielding the portion of the intermediate region comprises placing the metallic bag over the one or more loops.

In example 3, the method according to example 1, wherein the RF shield comprises a flexible metallic sleeve, and selectively shielding the one or more loops comprises sliding the flexible metallic sleeve over the portion of the intermediate region.

In example 4, the method according to any of examples 1-3, wherein selectively shielding the one or more loops of the lead comprises placing the RF shield over the intermediate region, and wherein the method further comprises removing the RF shield from over the intermediate region while leaving the lead implanted within the patient.

In example 5, the method according to example 1, wherein the lead comprises a polymeric body defining an exterior surface of the lead, the RF shield is a layer of metallic material deposited on the exterior surface only along the portion of the lead, and selectively shielding the one or more loops of the lead comprises coiling the portion of the lead on which the layer of metallic material is deposited into the one or more loops.

In example 6, the method according to any of examples 1-5, wherein the RF shield includes an identification tag indicating MRI conditional compatibility, and the method further comprises transcutaneously reading the indication of MRI conditional compatibility from the identification tag while the lead is implanted in the patient.

In example 7, the method according to any of examples 1-6, wherein the lead is implanted along the lead in the selectively shielding step such that no portion of the RF shield extends into the vasculature of the patient.

In example 8, the method according to any of examples 1-7, wherein the lead is shielded in the selectively shielding step such that only the one or more loops are shielded by the RF shield.

In example 9, the method according to any of examples 1-8, further comprising suturing the RF shield to one or both of fix the RF shield in position over the lead and anchor the RF shield at an implant location.

In example 10, an implantable lead having a distal region, a proximal region, and an intermediate region therebetween, the lead comprising at least one electrode disposed on the distal region of the lead. The lead can further include at least one conductor extending from the proximal region to the distal region, the at least one conductor electrically coupled to the at least one electrode, respectively. The lead can further include a polymeric body radially surrounding the at least one conductor, the polymeric body extending from the proximal region to the distal region, the polymeric body configured to electrically insulate the at least one conductor. The lead can further include an RF shield surrounding an outer surface of the polymeric body and only along the intermediate region of the elongated member, the lead configured to be coiled into one or more loops along the intermediate region, the RF shield configured to reduce RF signal coupling to the at least one conductor along the one or more loops.

In example 11, the lead of example 10, wherein the RF shield is selectively moveable over the intermediate region.

In example 12, the lead of either of examples 10 or 11, wherein the RF shield includes at least one of a metallic film and a metallic mesh.

In example 13, the lead of any of examples 10-12, wherein the RF shield comprises a metallic bag configured to envelope the one or more loops.

In example 14, the lead of any of examples 10-12, wherein the RF shield comprises a sleeve configured to slide over the lead.

In example 15, the lead of example 1, wherein the RF shield comprises a metallic layer deposited on an exterior surface of the polymeric body.

In example 16, the lead of any of examples 10-15, wherein the RF shield only shields the one or more loops of the lead.

In example 17, the lead of any of examples 10-14 or 16, wherein the RF shield is configured to be removed from the lead after implantation while allowing the lead to remain implanted.

In example 18, the lead of any of examples 10-17, wherein the RF shield includes a remotely readable identification tag indicating magnetic resonance conditional usage.

In example 19, an implantable lead comprising a lead body, the lead body configured to be coiled into one or more loops. The lead can further comprise at least one electrode and at least one conductor extending within the lead body, the at least one conductor electrically coupled to the at least one electrode, respectively. The lead can further comprise an RF shield, the RF shield moveable over the lead body and removable from the lead body, the RF shield configured to surround the one or more loops and reduce RF signal coupling to the at least one conductor along the one or more loops.

In example 20, the lead of example 19, wherein the RF shield only shields the one or more loops of the lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
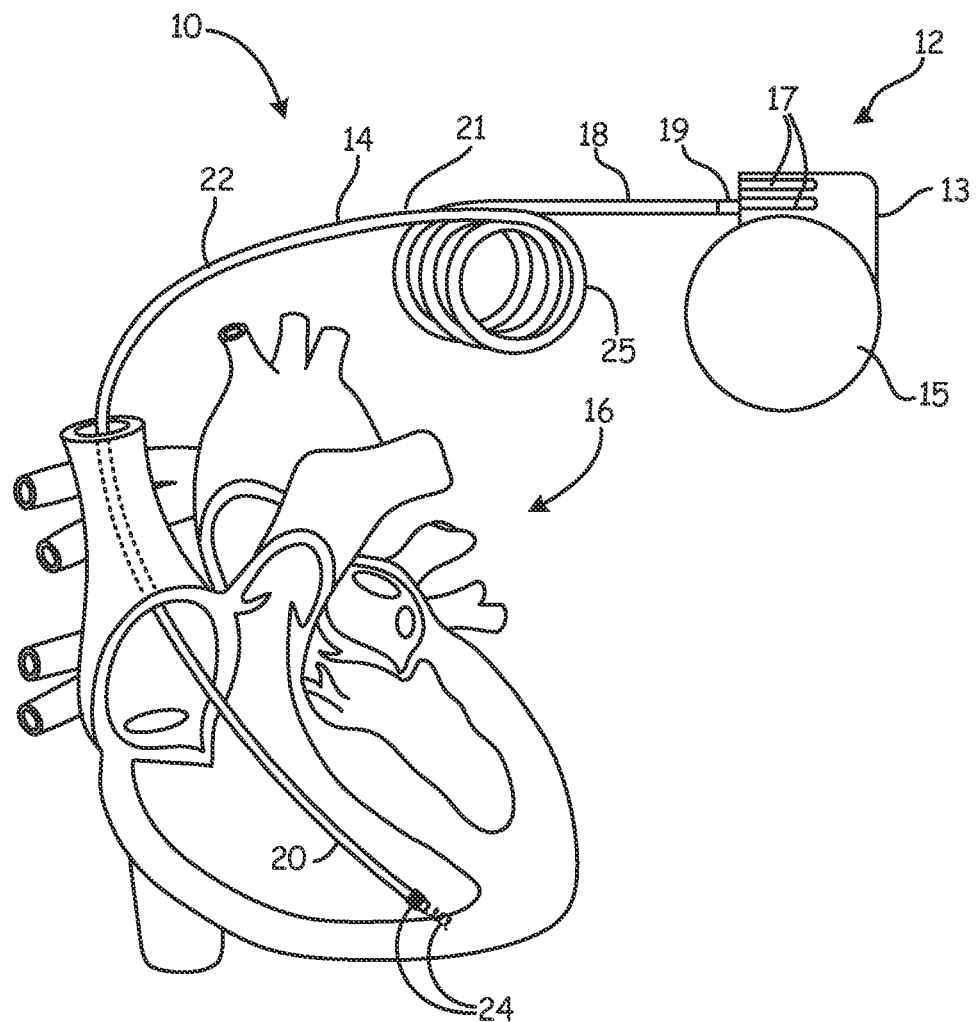
FIG. 1 is a combined cutaway view of a heart and a perspective view of a pulse generator and a lead.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As explained in further detail below, various embodiments of the present invention relate to cardiac rhythm management (CRM) systems incorporating lead shielding features adapted for operation in a MRI environment.

Figure 2:
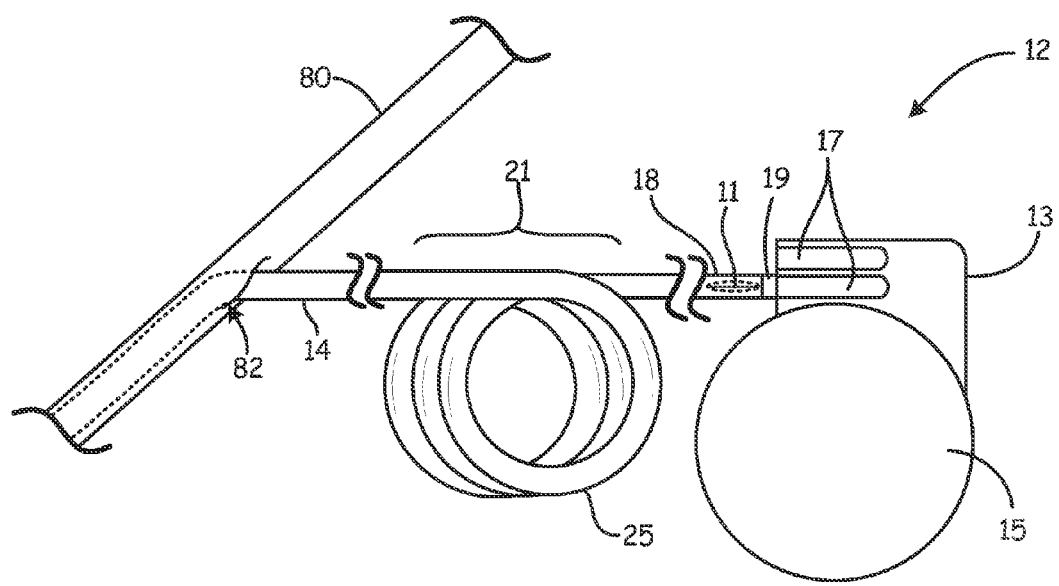
FIG. 2 is an isometric illustration of a proximal region of the pulse generator and the lead of FIG. 1.

FIG. 1 is a perspective view of an implantable medical device (IMD) 10 having a pulse generator 12 and a lead 14, and in particular shows the lead 14 implanted in the heart 16. FIG. 2 is a detailed view of the IMD 10, and in particular shows the lead 14 entering a vessel 80 at a vascular entry site 82. The lead 14 is an elongated member that operates to convey electrical signals between the heart 16 and the pulse generator 12. The lead 14 has a proximal region 18, a distal region 20, and an intermediate region 21 between the proximal region 18 and the distal region 20. The proximal region 18 is shown as coupled to the pulse generator 12. The proximal region 18 can comprise a connector having one or more contacts for electrically connecting with one or more channels of the pulse generator 12. One or more electrodes 24 can be disposed on the distal region 20. The one or more electrodes 24 can be configured to receive bioelectrical signals and/or apply stimulation therapy to tissue (e.g., cardiac tissue). A distal most one of the one or more electrodes 24 is shown as being an extendable/retractable fixation helix configured to secure the distal region 20 of the lead 14 within the heart 16. Such an extendable/retractable fixation helix may be absent in various other embodiments. As shown, no electrodes are provided along the intermediate region 21, however various other embodiments may include electrodes along the intermediate region 21. In various alternative embodiments, the lead 14 can be configured as a neural lead that includes an electrode cuff for coupling the lead 14 to a nerve. In some other embodiments, the lead 14 can be configured for epidural insertion to stimulate nerves of the spinal cord. It will be understood that other therapy applications of the lead 14 are possible.

The lead 14 includes a lead body 22. The lead body 22 can be formed by polymer insulative material. The polymeric insulative material of the lead body 22 can extend from the proximal region 18 (e.g., from the connector 19), through the intermediate region 21, to the distal region 20 of the lead 14. The lead body 22 can include an exterior surface that defines a substantial majority or all of the exterior surface of the lead 14, such as an exterior surface of the lead 14 that extends from the proximal region 18 to the distal region 20. The polymeric insulative material can comprise, for example, one or more of silicone rubber, polyurethane, polytetrafluoroethylene (PTFE), expanded tetrafluoroethylene (eTFE), or another suitable non-conductive material. In various embodiments, respective segments of the lead body 22 are made from different types of insulative material so as to tailor the lead body 22 characteristics to its intended clinical and operating environments. In various embodiments, different sections of the lead body 22 are made from different materials selected to provide desired functionalities.

Electrical signals can be carried between the pulse generator 12 and the one or more electrodes 24 by one or more conductors 11 extending through the lead 14 within the lead body 22 as shown in the cutaway of FIG. 2. The one or more conductors can be electrically coupled to one or more contacts of the connector 19. The conductors can be surrounded by the polymeric insulative material of the lead body 22 to insulate the conductors from tissue of the patient. The lead 14 or any other device of the present disclosure can comprise any feature disclosed in U.S. patent application Ser. No. 14/015,972, to Walker et al., and/or in U.S. Patent Pub. No. 2011/0160819 to Kunkel at al., each of which is hereby incorporated herein by reference in its entirety. While a single lead 14 is shown in FIG. 1, two or more leads may alternatively be connected to the pulse generator 12.

The pulse generator 12 may be any implantable medical device known in the art or later developed for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities. Additionally or alternatively, the pulse generator 12 can be configured for applying stimulation to a nerve via the lead 14. The lead 14 can be configured to convey electrical signals between the pulse generator 12 and the heart 16 or other target tissue. For example, in those embodiments in which the pulse generator 12 is a pacemaker, the lead 14 can be utilized to deliver electrical stimuli for pacing the heart 16. In those embodiments in which the pulse generator 12 is an implantable cardiac defibrillator, the lead 14 can be utilized to deliver electric shocks to the heart 16 in response to an event such as a heart attack or arrhythmia, in which case one or more coil electrodes may be provided along the distal region 20. In some embodiments, the pulse generator 12 includes both pacing and defibrillation capabilities.

The pulse generator 12 can include a connector header 13 that couples the pulse generator 12 to the connector 19 of the lead 14. The connector header 13 can have one or more bores 17 configured to receive the connector 19 on the proximal region 18 of the lead 14. As is known, one or more electrical contacts of the connector header 13 can respectively couple with lead contacts (not illustrated) of the connector 19 to electrically connect one or more channels of the pulse generator 12 to one or more conductors 11 and one or more electrodes 24 of the lead 14. The connector header 13 can be attached to a hermetically sealed enclosure 15 that contains a battery, electronic circuitry, and other commonly known components of a pulse generator 12.

The lead 14 can be susceptible to various hazards associated with the RF fields generated by MRI scanners inductively coupling with the one or more conductors 11. The one or more conductors 11 can unintentionally function as an antenna by picking up the RF signals and transmitting RF energy to the tissue at an interface with the electrode 24 which may lead to elevated temperatures and/or release of currents at the point to contact between the electrode 24 and tissue. The energy can additionally or alternatively travel back to a pulse generator 12 to damage circuitry and/or be erroneously interpreted as bioelectrical signals.

The pulse generator 12 can be implanted subcutaneously at an implantation location (e.g., a pocket) in the patient's chest or abdomen. The pulse generator 12 may alternatively be implanted along the patient's back or buttocks, such as with neural stimulation applications. As shown in FIG. 1, the lead 14 extends from an implant site of the pulse generator 12 to an implant site of the distal region 20 of the lead 14. The lead 14 enters the vasculature via a vascular entry site 82 of a vessel 80. The vessel 80 may be the left subclavian vein. Alternative entry sites for a lead include the right subclavian vein, the left axillary vein, the left external jugular, the left internal jugular, and the left brachiocephalic vein, among other options.

Leads 14 are generally manufactured only in a limited number of lead lengths. The full length of the lead 14 may not be needed to bridge between the implant site of the pulse generator 12 to the implant site of the distal region 20 of the lead 14. Excess lead length (e.g., the length beyond that needed to reach from the implant site of the pulse generator 12 to the implant site of the distal region 20) can be coiled to form a coiled portion 25. The coiled portion 25 comprises one or more loops of the lead 14 between the implant site of the pulse generator 12 and the vascular entry site 82. The number of loops and/or the radius of the loops can be set by the implanting clinician to adjust the effective length of the lead 14 that bridges between the implant site of the pulse generator 12 and the vascular entry site 82 or the implant site of the distal region 20 of the lead 14. The coiled portion 25 can be placed in a subcutaneous pocket near the pulse generator 12.

The coiled portion 25 of the lead 14 can have an increased susceptibility to RF inductive coupling versus the straight portions of the lead 14. The coiled portion 25 can be susceptible to RF inductive coupling due to constructive interference from the one or more conductors 11 of the lead 14 wound or looped upon itself multiple times. Furthermore, the coiled portion 25 can be particularly susceptible to RF inductive coupling and excessive heating associated with MRI environments due to the placement of the coiled portion 25 in subcutaneous pockets near the periphery of the patient's body. According to patient models of specific absorption rates (SAR) during MRI imaging studies, tissue heating and RF interference is localized at the periphery of a patient's body, such as at the arms and the edges of the thoracic cavity. The pulse generator 12 and the coiled portion 25 are typically positioned in or near the edges of the thoracic cavity and are therefore at increased risk of RF coupling and excessive heating associated with MRI environments. Addressing the particular susceptibility of the coiled portion 25 to inducted RF energy can allow for the use of existing lead designs (e.g., without further shielding or other features configured to mitigate the effects of RF fields) in MRI environments. Selective shielding of the coiled portion 25 and/or other portions of the lead 14 are further discussed herein.

Various embodiments of the present disclosure relate to providing an RF shielding layer over a portion of the lead 14 to suppress RF signal coupling to the lead 14 to significantly reduce the potential for lead heating and other hazards. In various embodiments, the RF shielding is provided only along a portion of the intermediate region 21 of the lead body 22. In some embodiments, the RF shielding is provided only over the coiled portion 25 of the lead body 22. The RF shielding may cover the entirety of the coiled portion 25. The RF shielding may cover the entirety of the coiled portion 25 while not covering any other section of the lead body 22 (e.g., the RF shield may not extend along the lead 14 distally or proximally of the coiled portion 25). Various RF shield configurations are further discussed herein in connection with FIGS. 3A-5.

Figure 3A:
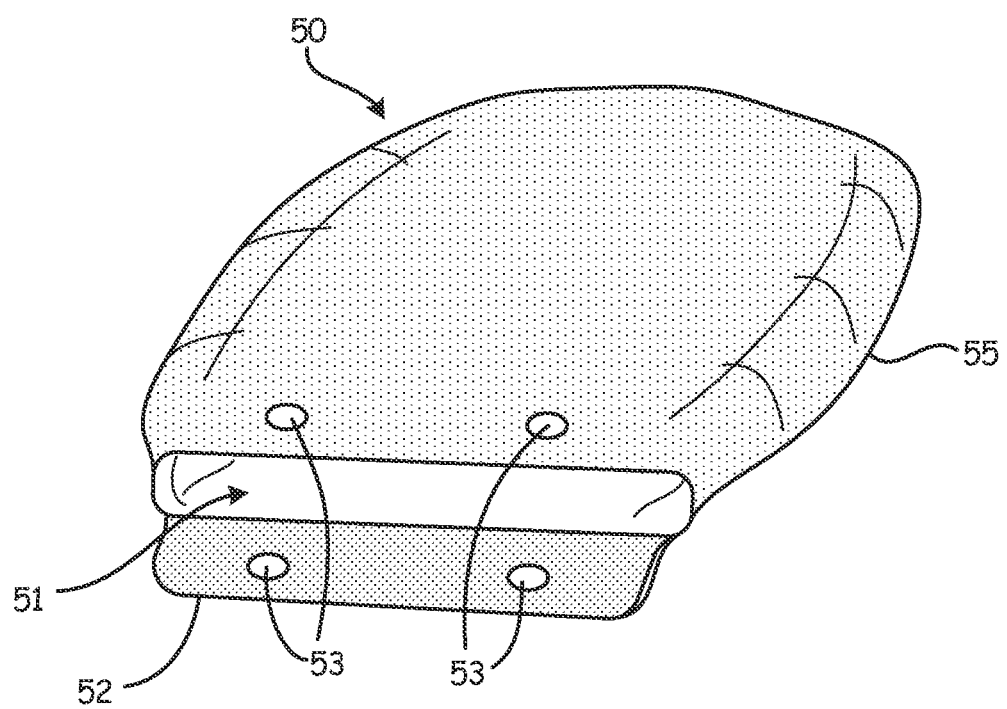
FIG. 3A is an isometric illustration of an RF shield bag.

FIG. 3A shows a perspective view of a bag 50. The bag 50 can be formed partially or entirely by metallic material. The bag 50 comprises a main body 55 having an interior space which can accommodate a portion of the lead 14 (e.g., the coiled portion 25) therein. The bag 50 comprises an opening 51. The opening 51 provides access to the interior space of the main body 55, the interior space otherwise being substantially or fully closed by the main body 55. The opening 51 may be the only opening in the bag 50 large enough to accommodate passage of the coiled portion 25. In some embodiments, the opening 51 may be the only opening in the bag 50 that has an inner diameter that is larger than the outer diameter of the lead 14. In other words, the opening 51 may be the only hole in the bag 50 large enough to accommodate passage of the lead body 22. The bag 50 can include a flap 52. The flap 52 can bend over the opening 51 to partially or fully close the opening 51 to enclose the interior space within the bag 50. As shown, the flap 52 and the main body 55 can include holes 53. The holes 53 may align when the flap 52 is closed over the main body 55. The holes 53 can be large enough in diameter to accommodate suturing 54 through the holes 53 for anchoring the bag 50 and/or closing the flap 52 as shown in FIG. 3B.

Figure 3B:
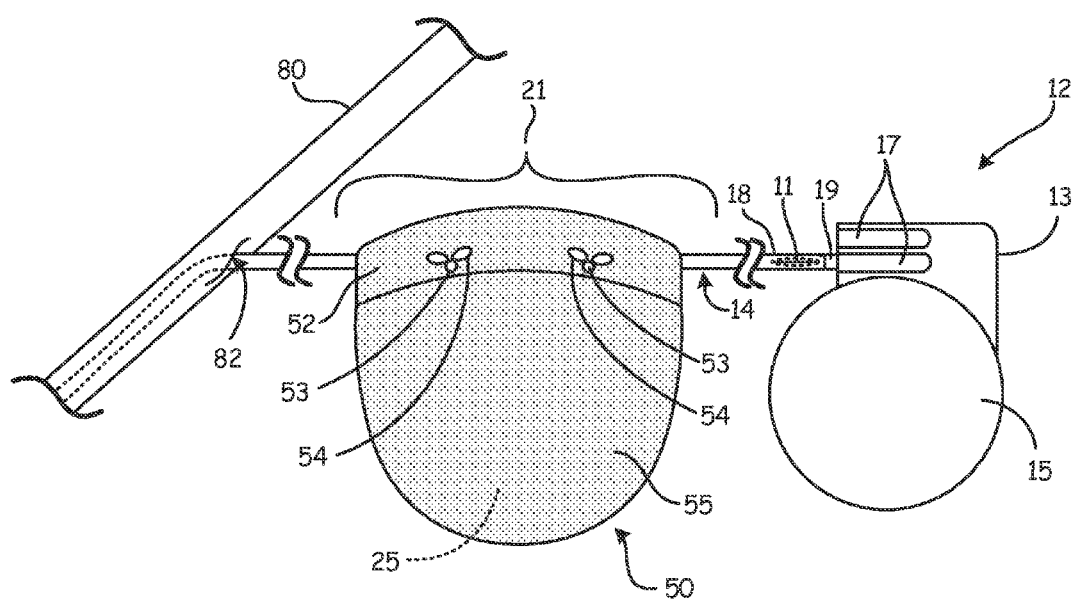
FIG. 3B is an isometric illustration of the RF shield bag of FIG. 3A on a selected portion of the lead of FIGS. 1 and 2.

FIG. 3B is an isometric illustration of the bag 50 over the coiled portion 25 of the lead 14. As shown, a portion of the intermediate region 21 of the lead 14 forming the coiled portion 25 can be contained within the bag 50. The bag 50 can fully envelope the coiled portion 25, including the empty space at the center of loops of the lead 14. The coiled portion 25 can be contained within the interior space of the main body 55. The flap 52 can cover the opening 51 to secure the coiled portion 25 within the bag 50. Sutures 54 can extend though the holes 53 to fasten the flap 52 closed over the opening 51. In addition or as an alternative to the flap 52, the bag 50 may include a purse string closure around the opening 51 to secure the coiled portion 25 within the bag 50. As shown in FIG. 3B, the lead 14 can extend proximally and distally of the bag 50 from proximal and distal ends of the opening 51.

The bag 50 may be constructed of a biocompatible material including at least one of a metallic film material, a metallic mesh material, a polymer substrate with a solid and/or patterned metallic layer disposed thereon (e.g., a pattern of metallic dots), a non-metallic substrate doped with metallic particles, and any combination thereof. The metallic material of the bag 50 can allow the bag 50 to function as a Faraday shield or cage which disrupts inductive coupling to the one or more conductors 11 of the lead 14 extending along the coiled portion 25. As shown, the bag 50 has a rounded outer profile with no corners. In this way, the bag 50 can minimize or eliminates sharp corners or edges which can otherwise become MRI heating hotspots. The bag 50 may include an antimicrobial agent.

The bag 50 is moveable with respect to the lead 14 to selectively cover a portion of the lead 14. Preferably, the bag 50 covers the coiled portion 25 of the intermediate region 21. The bag 50 is electrically isolated from all electrical conductors of the lead 14 so as to not conduct RF energy to the lead 14. The bag 50 may not be in direct contact with the blood pool in the vasculature of the patient to prevent conduction of RF energy or heat to these tissues. The bag 50 is located such that it is not in electrical contact with the heart 16 tissue, and is preferably not located close to the heart, so as to not conduct induced RF energy to the heart.

The bag 50 can be introduced into a patient at the same time as implantation of the lead 14 or at some later time (e.g., in a separate surgical procedure days or years after the implantation of the lead 14). One advantage of the bag 50 is that such a device can be used on previously implanted leads which may not be configured to be safely used in an MRI environment (e.g., not engineered to be labeled as MRI conditionally safe). For example, if a patient with a previously fitted lead 14 that is not labeled for MRI conditional usage but is in need to undergo an MRI procedure, then a minimally invasive surgery can be performed to easily enclose the coiled portion 25 within the bag 50 and the patient may undergo the non-invasive MRI study without removal of the lead 14. Furthermore, the bag 50 is removable after the MRI study is complete while the lead 14 is implanted. Alternatively, the bag 50 may be left in place for the life of the lead 14. While a bag 50 is shown and described, any other type of metallic container may be provided to partially or fully envelope a portion of the intermediate region 21 of the lead 14, including the coiled portion 25.

Figure 4A:
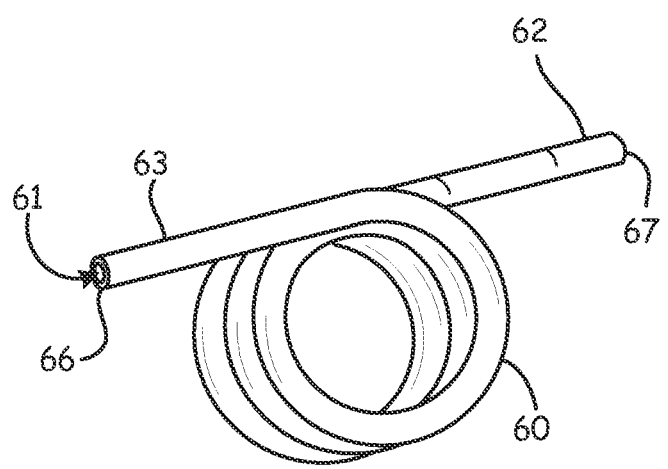
FIG. 4A is an isometric illustration of an RF shield sleeve.
Figure 4B:
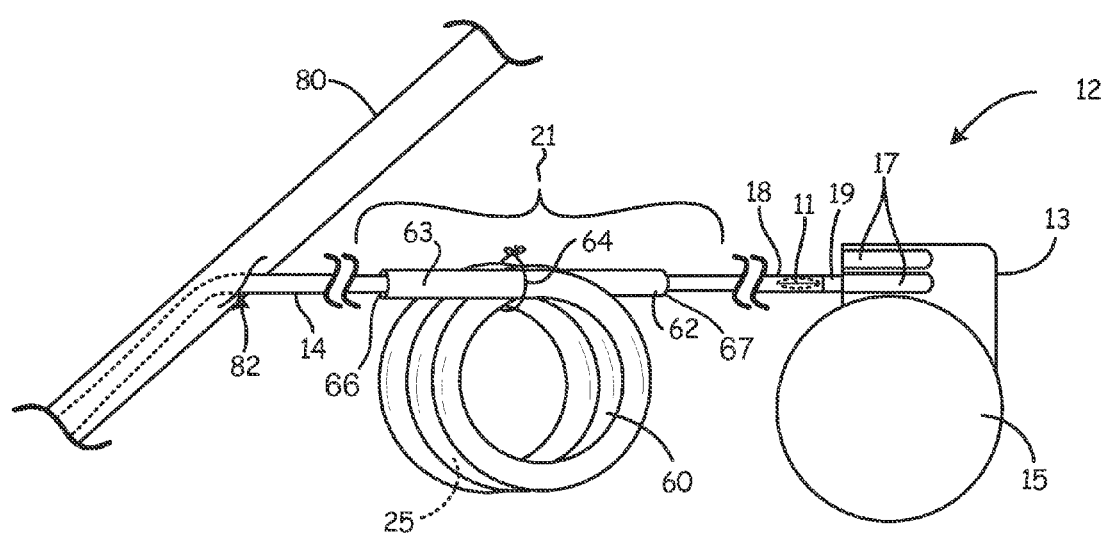
FIG. 4B is an isometric illustration of the RF shield sleeve of FIG. 4A on a selected portion of the lead of FIGS. 1 and 2.

FIG. 4A shows a perspective view of a sleeve 60. The sleeve 60 comprises an elongated tube having a lumen 61 with a distal opening 66 and a proximal opening 67. FIG. 4B shows a perspective view of the sleeve 60 on the lead 14. The lumen 61 of the sleeve 60 can accommodate a portion of the intermediate region 21 of the lead 14 (e.g., the coiled portion 25) within the lumen 61. The inner diameter of the lumen 61 may be larger than the outer diameter of the lead 14 to allow the sleeve 60 to be slid over the lead 14 to selectively shield a section of the lead 14. As shown, the coiled portion 25 of the intermediate region 21 of the lead 14 is contained within the lumen of the sleeve 60, thereby shielding the one or more conductors 11 within the coiled portion 25 from RF energy associated with MRI scans. The sleeve 60 can fully envelope the coiled portion 25 while leaving the empty space at the center of loops of the lead 14 unshielded. As shown in FIG. 4B, the lead 14 can extend proximally from the proximal opening 67 of the sleeve 60 and distally from the distal opening 66 of the sleeve 60. In some embodiments, the sleeve 60 may only cover the coiled portion 25 of the lead 14 and may not extend along the lead 14 distally or proximally of the coiled portion 25. As also shown in FIG. 4B, the sleeve 60 may only cover a portion of the intermediate region 21 corresponding to the coiled portion 25 and may not cover either of the proximal region 18 or the distal region 20. The sleeve 60 may be cutable during an implantation procedure to allow the length of the sleeve 60 to be customized to accommodate the length of excess lead 14.

The sleeve 60 may comprise at least one of a metallic film material, a metallic mesh material, a polymer substrate with a solid and/or patterned metallic layer disposed thereon (e.g., a pattern of metallic dots), a non-metallic substrate (e.g., polymer) doped with metallic particles, and any combination thereof. The sleeve 60 may include an antimicrobial agent. The metallic material of the sleeve 60 can allow the sleeve 60 to function as a Faraday shield or cage which disrupts inductive coupling to any conductors of the lead 14 extending underneath the coiled portion 25 within the lead body 22. The sleeve 60 can be electrically isolated from all electrical conductors of the lead 14 so as to not conduct RF energy to the lead 14. The electrical isolation forces inducted RF energy to dissipate locally along the sleeve 60 and avoids concentrated RF energy dissipation to tissue associated with hazardous hot spots.

The sleeve 60 is located such that it is not in electrical contact with the heart 16 tissue, and is preferably not located close to the heart, so as to not conduct inducted RF energy to the heart. The sleeve 60 may not be in direct contact with the blood pool in the vasculature of the patient to prevent conduction of RF energy or heat to these tissues. It may be preferable to not have the sleeve 60 extend into the vessel 80 so as to prevent inducted RF energy and associated heat from traveling into the patient's blood pool. As shown in FIG. 4B, the distal end 63 of the sleeve 60 terminates proximally of the vascular entry site 82. In some other embodiments, the distal end 63 of the sleeve 60 terminates proximate of the vascular entry site 82 without entering the vessel 80. For example, the distal end 63 of the sleeve 60 can terminate within 5 centimeters of the vascular entry site 82. In various embodiments, the distal end 63 terminates the sleeve 60 at the vascular entry site 82 without the sleeve 60 entering the vessel 80. In some embodiments, the sleeve 60 may extend only a limited distance into the vessel, such as 5 centimeters past the vascular entry site 82. The proximal end 62 of the sleeve 60 terminates distally of the connector 19 so as to not conduct inducted RF energy and associated heat to the pulse generator 12.

The sleeve 60 can be introduced into a patient at the same time as implantation of the lead 14 or at some later time (e.g., in a separate surgical procedure days or years after the implantation of the lead 14). The sleeve 60 can be slide over the lead 14 before any part of the lead 40 is introduced into the patient. Alternatively, one part of the lead can be implanted at an implant location before the sleeve 60 is slid over another part of the lead 14. For example, the distal region 20 of the lead 14 can be implanted in the heart 16 while the proximal region 18 of the lead 14 can extend partially or fully out of the patient to interface with a pacing system analyzer (not illustrated). While the distal region 20 of the lead 14 is implanted, and when neither of the pacing system analyzer nor the pulse generator 12 are connected to the lead 14, the sleeve 60 can be slid over the proximal region 18 of the lead 14 and advanced to the intermediate region 21. The proximal region 18 of the lead 14 can then be connected to the pulse generator 12 and implantation of the lead 14 and the pulse generator 12 can be completed. In some cases, the intermediate region 21 may be formed into the coiled portion 25 before the sleeve 60 is slid over the intermediate region 21 or optionally any other part of the lead 14. In such a case, the sleeve 60 assumes a coiled configuration having one or more loops when advanced over the coiled portion 25. In some other cases, the intermediate region 21 may be generally straight or at least not coiled when the sleeve 60 is advanced over the intermediate region 21. The intermediate region 21 of the lead 14 and the sleeve 60 can then be coiled to form loops to define the coiled portion 25.

A suture 64 can wrap around one, multiple, or all loops of the sleeve 60 and the lead 14. The sleeve 60 may be fixed to the lead 14 by suture 64. For example, the suture 64 may be tightly wound around the exterior of the sleeve 60 such that the lumen 61 of the sleeve 60 pinches the lead 14. The suture 64 can prevent uncoiling of the lead 14 and the sleeve 60. The suture 64 can penetrate tissue to anchor the sleeve 60 and the coiled portion 25 of the lead 14 at a preferred implant site.

The sleeve 60 can be placed on previously implanted leads. The previously implanted lead 14 may not be configured to be safely used in an MRI environment and may not be labeled as MRI conditionally safe. For example, a patient with a previously fitted lead 14 that is not labeled for MRI conditional usage may undergo an MRI procedure by disconnecting the connector 19 from the pulse generator 12 and then sliding the sleeve 60 over the lead 14. Following the MRI procedure, the sleeve 60 may be removed from the lead 14 or may be left in place for the life of the lead 14. In some embodiments, the sleeve 60 may include a slit that extends from the proximal end 62 to the distal end 63 of the sleeve 60 and allows the sleeve 60 to be fit over and/or removed from the lead body 22 of a previously implanted lead 14. With such a slit, the sleeve 60 can fit over a portion of the lead 14 while the distal region 20 remains at an implant site and the proximal region 18 remains connected to the pulse generator 12. A sleeve 60 having a slit can be fit over a previously implanted lead 14 just prior to an MRI procedure and optionally removed following the MRI procedure while leaving the lead 14 implanted.

Figure 5:
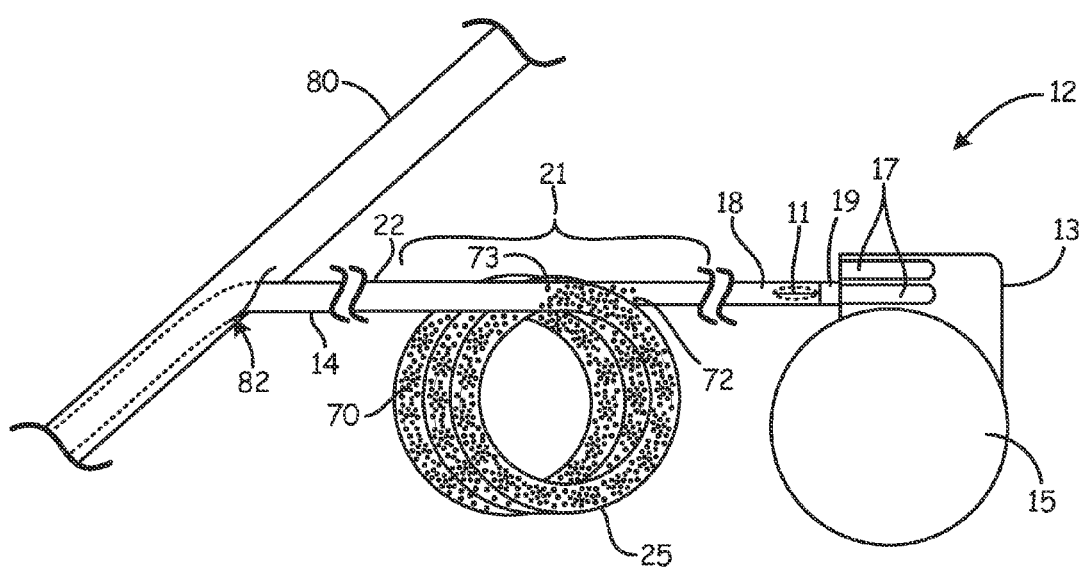
FIG. 5 is an isometric illustration of an RF shield layer on a selected portion of the lead of FIGS. 1 and 2.

FIG. 5 is an isometric illustration of the RF shield according to various embodiments. As shown in FIG. 5, the RF shield can be a deposited RF shield layer 70 deposited onto the outer surface of the lead body 22. The deposited RF shield layer 70 can extend along a lead body 22 as a section having a proximal end 72 and a distal end 73. The deposited RF shield layer 70 is represented in FIG. 5 by a dotted pattern on the exterior surface of the lead 14 extending from the proximal end 72 to the distal end 73. The location of the deposited RF shield layer 70 along the lead 14 can be limited to the intermediate region 21 such that the deposited RF shield layer 70 does not extend along the lead 14 along the proximal region 18 or the distal region 20. More specifically, the deposited RF shield layer 70 can be present only on the coiled portion 25 such that the deposited RF shield layer 70 does not extend along the lead 14 distally or proximally from the coiled portion 25. The particular section of the intermediate region 21 on which the deposited RF shield layer 70 may be deposited can be determined based on the length of the available lead 14 and the anatomical dimensions of the patient or based on a priori anatomical models of various patient sizes and/or dimensions.

During an implantation procedure, a clinician may identify which section of the lead 14 is shielded by the deposited RF shield layer 70 and then coil that section to form the coiled portion 25 while purposefully not using any other sections of the lead 14 that is unshielded by the deposited RF shield layer 70 to form the coiled portion 25. In this way, the clinician selectively uses the RF shielded section of the lead 14 for forming the coiled portion 25. The section along which the deposited RF shield layer 70 is deposited may appear visually different relative to sections of the lead body along which the deposited RF shield layer 70 is not deposited due to the presence or absence of the deposited RF shield layer 70 to aid in determining which section to coil. In some cases, a marking (e.g., a colored stripe) may be visible on the exterior surface of the lead body 22 indicating the longitudinal extent of the deposited RF shield layer 70 to assist the clinician in determining which section of the lead 14 is shielded.

The conductive RF layer can be a pattern of metallic material deposited on the exterior surface of the lead 14. The exterior surface of the lead 14 can be defined by a polymeric lead body in various embodiments, and in such embodiments the deposited RF shield layer 70 can be a pattern of metallic material deposited on the polymeric exterior surface of the lead 14. The deposited RF shield layer 70 may be deposited using metallic sputtering. For example, a section of the intermediate region 21 can be coated with the deposited RF shield layer 70 by sputtering of metal material onto the exterior surface of the lead body 22 or a polymer subcomponent that will eventually define an exterior surface of the lead body 22. The deposited RF shield layer 70 can comprise a continuous layer of conductive material. The deposited RF shield layer 70 can be continuous from the proximal end 72 to the distal end 73 of the deposited RF shield layer 70. In this way, RF energy received by the deposited RF shield layer 70 can be conducted from the proximal end 72 to the distal end 73 of the deposited RF shield layer 70. The deposited RF shield layer 70 can alternatively comprise electrically isolated elements such as rings or dots. Such a pattern will not conduct RF energy received by the deposited RF shield layer 70 between the proximal end 72 and the distal end 73 of the deposited RF shield layer 70. The deposited RF shield layer 70 can be deposited around the entire circumference of the lead 14 along the full length of the section of the lead 14 targeted for shielding. The deposited RF shield layer 70 can be exposed on the outer surface of the lead 14 to define part of the exterior of the lead 14. The deposited RF shield layer 70 can comprise gold or other biocompatible metal. In some embodiments, a polymer coating can be deposited over the deposited RF shield layer 70 to prevent tissue from contacting the deposited RF shield layer 70. In such case, copper or other generally non-biocompatible metal can be used for the deposited RF shield layer 70.

The deposited RF shield layer 70 may not be electrically connected to any electrical conductors of the lead 14 (e.g., conductors that electrically connect with electrodes 24). Such isolation prevents unwanted conduction of MRI energy to other areas of the lead 14. The deposited RF shield layer 70 shields a section of the one or more conductors 11 within the lead body 22 that is underneath the deposited RF shield layer 70 to prevent RF fields generated by an MRI scanner from inductively coupling with the one or more conductors 11 underneath the deposited RF shield layer 70.

The deposited RF shield layer 70 is located such that it is not in electrical contact with the heart 16 tissue, and is preferably not located close to the heart, so as to not conduct inducted RF energy to the heart. The deposited RF shield layer 70 may not be in direct contact with the blood pool in the vasculature of the patient to prevent conduction of RF energy or heat to these tissues. It may be preferable to not have the deposited RF shield layer 70 extend into the vessel 80 so as to prevent inducted RF energy and associated heat from traveling into the patient's blood pool. As shown in FIG. 5, the distal end 73 of the deposited RF shield layer 70 terminates proximally of the vascular entry site 82. In some other embodiments, the distal end 73 of the deposited RF shield layer 70 terminates proximate of the vascular entry site 82 without entering the vessel 80. For example, the distal end 73 of the deposited RF shield layer can terminate within 5 centimeters of the vascular entry site 82. In various embodiments, the distal end 73 terminates the deposited RF shield layer 70 at the vascular entry site 82 without the deposited RF shield layer 70 entering the vessel 80. In some embodiments, the deposited RF shield layer 70 may extend only a limited distance into the vessel, such as 5 centimeters past the vascular entry site 82. The proximal end 72 of the deposited RF shield layer 70 terminates distally of the connector 19 so as to not conduct inducted RF energy and associated heat to the pulse generator 12.

Any RF shield disclosed herein (e.g., the bag 50, the sleeve 60, the deposited RF shield layer 70) can include an identification tag integrated into the RF shield. The identification tag can include transcutaneously readable data indicating MRI conditional usage. The RF shield indicating conditional MRI compatibility allows an MRI procedure to go forward even though it may be known that the lead 14 alone is not configured to be MRI conditionally compatible. For example, the RF shield may include an X-ray identifiable marker which includes MRI conditional usage information pertaining to the IMD 10 and/or the RF shield. Such a marker may include text defined by metallic material and readable by an imaging device. In various other embodiments, the RF shield may include at least one of an RF, acoustic, optical, or the like based identification tag which is remotely interrogatable ex vivo. When interrogated, the identification tag transmits MRI conditional usage data pertaining to the IMD 10 and/or the corresponding shield.

While shielding of a coiled portion 25 of a lead 14 is discussed herein, the RF shields disclosed herein may be used to cover and shield an uncoiled lead or an uncoiled section of a lead. In some embodiments, a suitable length of lead 14 is available for a particular patient such that no excessive lead length is available nor coiled. In this embodiment, one of the various shields disclosed herein may cover a substantially straight section (i.e. uncoiled section) of the intermediate region 21. The RF shield may not extend into a vessel 80 (e.g., past a vascular entry site 82) as discussed herein.

Various modifications can be made to the exemplary embodiments discussed without departing from the scope of the present invention, including by removing features and/or adding features of other embodiments. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of shielding an implantable lead, the method comprising:

implanting a lead in a patient, the lead having a distal region, a proximal region, an intermediate region between the distal region and the proximal region, at least one electrode disposed on the distal region, and at least one conductor extending from the proximal region to the at least one electrode;

coiling a portion of the intermediate region to define one or more loops; and selectively shielding the one or more loops of the lead with an RF shield, the RF shield comprising metallic material and configured to reduce RF signal coupling to the at least one conductor along the one or more loops.

2. The method of claim 1, wherein the RF shield comprises a metallic bag, and selectively shielding the portion of the intermediate region comprises placing the metallic bag over the one or more loops.

3. The method of claim 1, wherein the RF shield comprises a flexible metallic sleeve, and selectively shielding the one or more loops comprises sliding the flexible metallic sleeve over the portion of the intermediate region.

4. The method of claim 1, wherein the lead comprises a polymeric body defining an exterior surface of the lead, the RF shield is a layer of metallic material deposited on the exterior surface only along the portion of the lead, and selectively shielding the one or more loops of the lead comprises coiling the portion of the lead on which the layer of metallic material is deposited into the one or more loops.

5. The method of claim 1, wherein selectively shielding the one or more loops of the lead comprises placing the RF shield over the intermediate region, and wherein the method further comprises removing the RF shield from over the intermediate region while leaving the lead implanted within the patient.

6. The method of claim 1, wherein the RF shield includes an identification tag indicating MRI conditional compatibility, and the method further comprises transcutaneously reading the indication of MRI conditional compatibility from the identification tag while the lead is implanted in the patient.

7. The method of claim 1, wherein the RF shield is placed along the lead in the selectively shielding step such that no portion of the RF shield extends into the vasculature of the patient.

8. The method of claim 1, wherein the lead is shielded in the selectively shielding step such that only the one or more loops are shielded by the RF shield.

9. The method of claim 1, further comprising suturing the RF shield to one or both of fix the RF shield in position over the lead and anchor the RF shield at an implant location.

10. An implantable lead having a distal region, a proximal region, and an intermediate region therebetween, the lead comprising:

at least one electrode disposed on the distal region of the lead;

at least one conductor extending from the proximal region to the distal region, the at least one conductor electrically coupled to the at least one electrode, respectively;

a polymeric body radially surrounding the at least one conductor, the polymeric body extending from the proximal region to the distal region, the polymeric body configured to electrically insulate the at least one conductor; and an RF shield surrounding an outer surface of the polymeric body and only along the intermediate region of the elongated member, the lead configured to be coiled into one or more loops along the intermediate region, the RF shield configured to reduce RF signal coupling to the at least one conductor along the one or more loops.

11. The lead of claim 10, wherein the RF shield is selectively moveable over the intermediate region.

12. The lead of claim 10, wherein the RF shield includes at least one of a metallic film and a metallic mesh.

13. The lead of claim 10, wherein the RF shield comprises a metallic bag configured to envelope the one or more loops.

14. The lead of claim 10, wherein the RF shield comprises a sleeve configured to slide over the lead.

15. The lead of claim 10, wherein the RF shield comprises a metallic layer deposited on an exterior surface of the polymeric body.

16. The lead of claim 10, wherein the RF shield only shields the one or more loops of the lead.

17. The lead of claim 10, wherein the RF shield is configured to be removed from the lead after implantation while allowing the lead to remain implanted.

18. The lead of claim 10, wherein the RF shield includes a remotely readable identification tag indicating magnetic resonance conditional usage.

19. An implantable lead, the lead comprising:
   a lead body, the lead body configured to be coiled into one or more loops;
   at least one electrode;
   at least one conductor extending within the lead body, the at least one conductor electrically coupled to the at least one electrode, respectively; and
   an RF shield, the RF shield moveable over the lead body and removable from the lead body, the RF shield configured to surround the one or more loops and reduce RF signal coupling to the at least one conductor along the one or more loops.

20. The lead of claim 19, wherein the RF shield only shields the one or more loops of the lead.

* * * * *